United States Patent [19]
Grim et al.

[11] Patent Number: 5,445,602
[45] Date of Patent: Aug. 29, 1995

[54] FLEXIBLE ANKLE BRACE

[75] Inventors: Tracy E. Grim, Broken Arrow, Okla.; William K. Arnold, Longmeadow, Mass.; Joseph M. Iglesias, Agoura, Calif.

[73] Assignee: Royce Medical Company, Westlake Village, Calif.

[21] Appl. No.: 99,237
[22] Filed: Jul. 29, 1993
[51] Int. Cl.$^6$ ............................................. A61F 5/00
[52] U.S. Cl. ................................... 602/27; 602/6
[58] Field of Search ............................... 602/5–8, 602/13, 23, 27; 607/108, 111

[56] References Cited

U.S. PATENT DOCUMENTS

| | | |
|---|---|---|
| 4,161,175 | 7/1979 | Bentele .................................. 602/6 |
| 4,280,489 | 7/1981 | Johnson, Jr. . |
| 4,628,945 | 12/1986 | Johnson, Jr. . |
| 4,964,402 | 10/1990 | Grim et al. . |
| 4,977,891 | 12/1990 | Grim . |
| 5,007,416 | 4/1991 | Burns et al. .......................... 602/27 |
| 5,027,801 | 7/1991 | Grim . |
| 5,031,607 | 7/1991 | Peters .................................. 602/27 |
| 5,092,319 | 3/1992 | Grim .................................. 602/27 |
| 5,209,722 | 5/1993 | Miklaus et al. ...................... 602/27 |
| 5,361,955 | 11/1994 | Gregory ............................. 224/211 |

Primary Examiner—Linda C. M. Dvorak
Attorney, Agent, or Firm—Poms, Smith, Lande & Rose

[57] ABSTRACT

An improved ankle brace may have two relatively rigid side supports, the outer edge portion of the lower area of the side supports, adjacent to the ankle being covered with a flexible or resilient material. The flexible resilient material may be permanently secured to the side supports by bonding, mechanical interlocking, or by any other suitable arrangements. Additional resilient flexible material may be placed on the interior surface of the side supports to improve the fit and comfort of the brace around the user's lower leg. The rigid side supports may be of an open type with the resilient flexible material extending across the side supports and beyond the edges thereof.

21 Claims, 6 Drawing Sheets

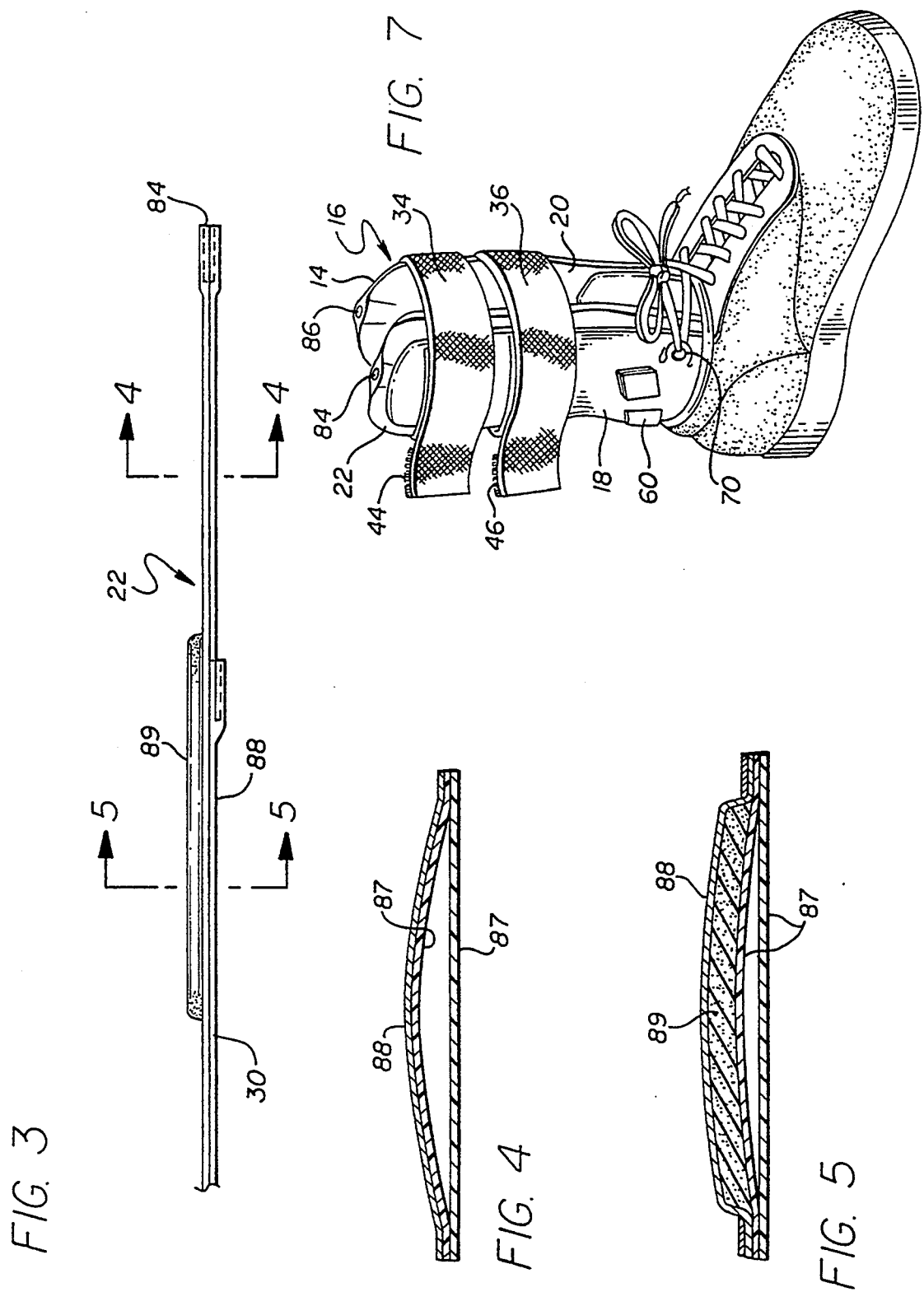

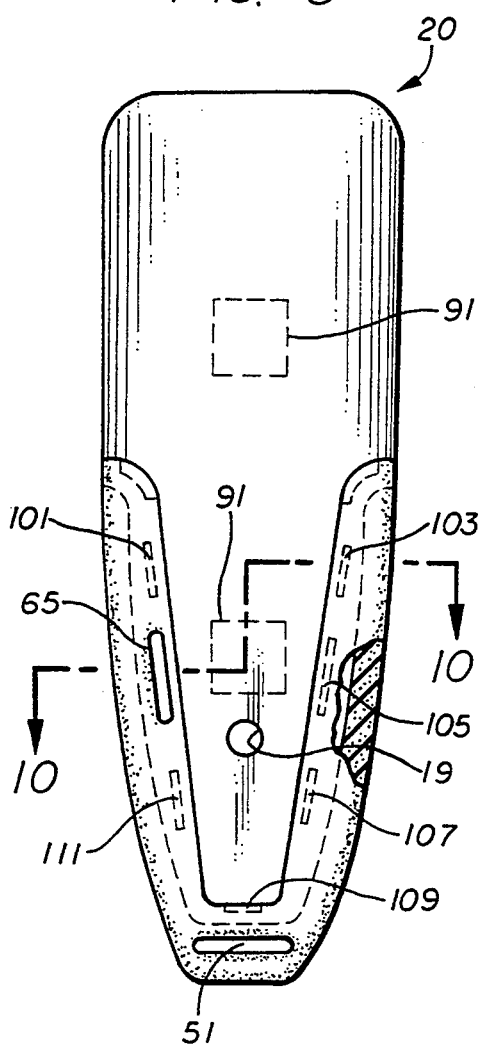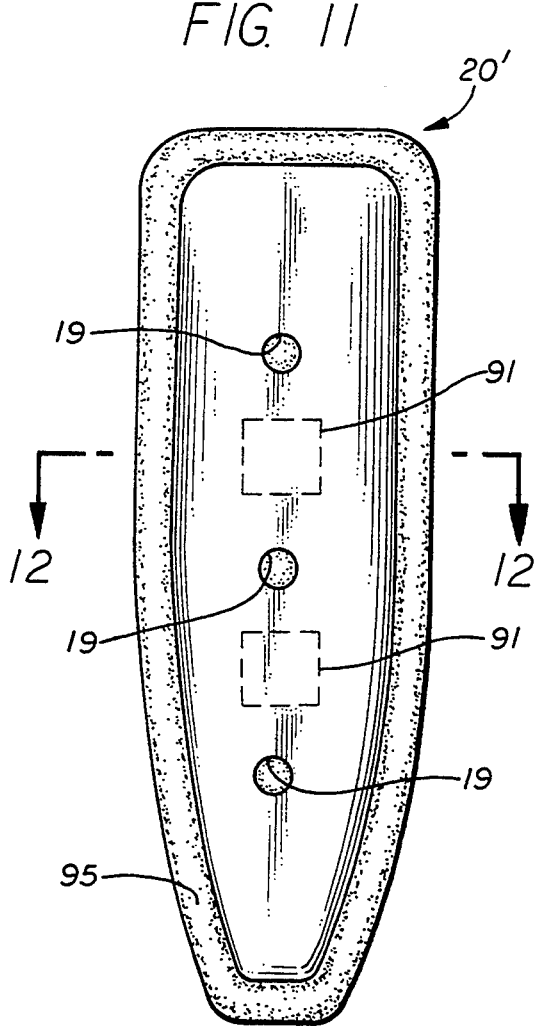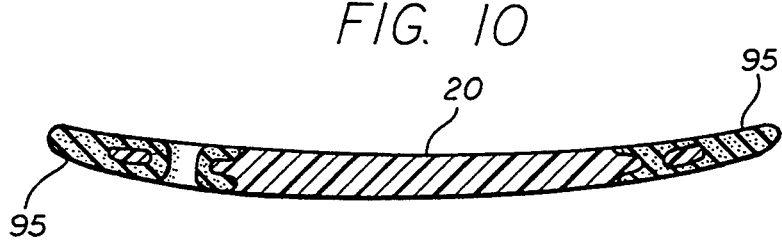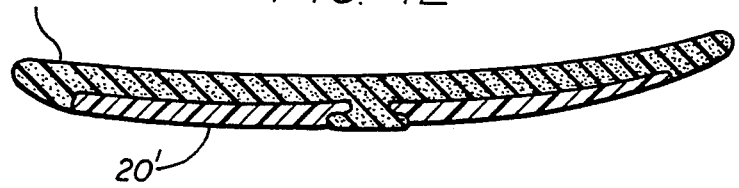

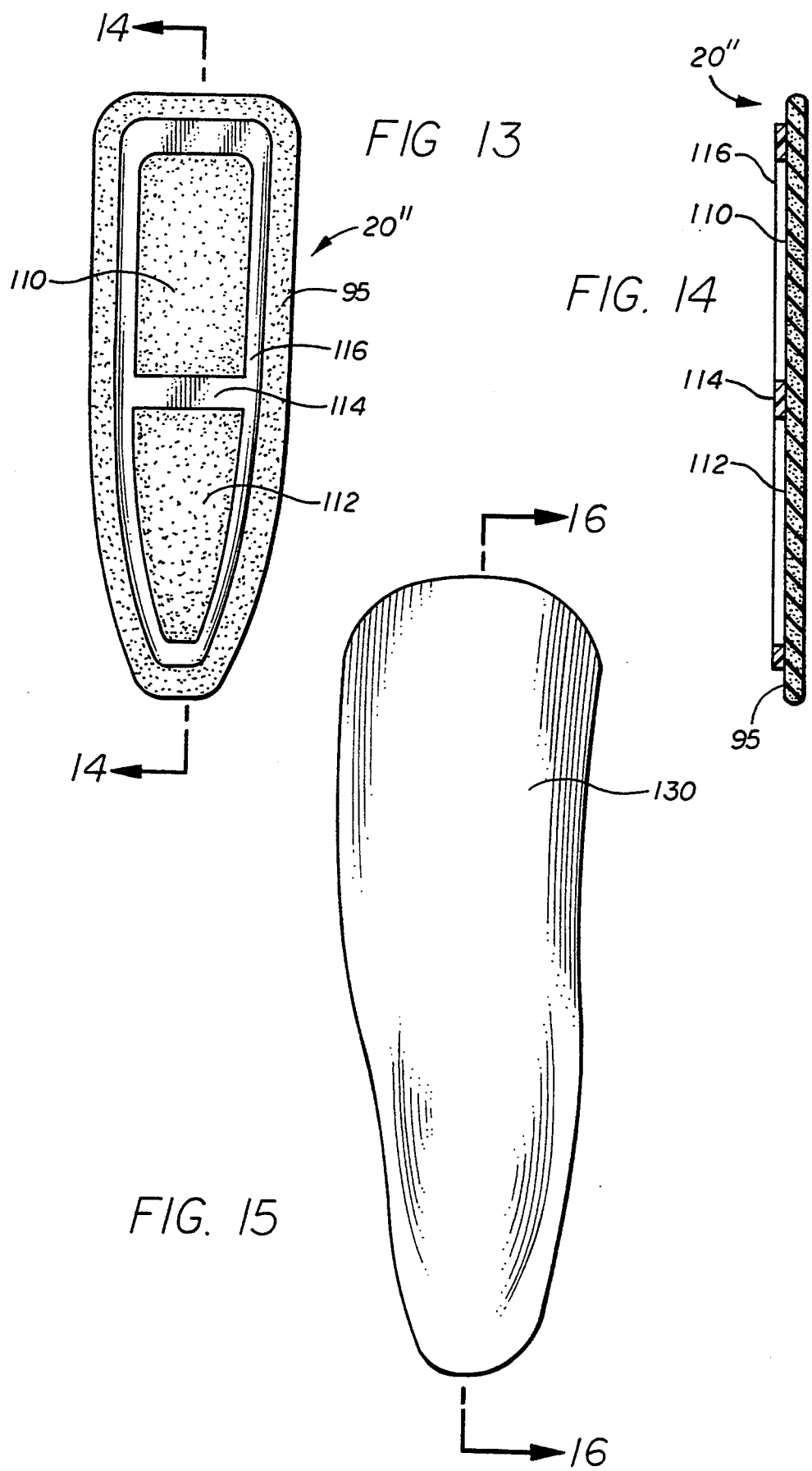

FLEXIBLE ANKLE BRACE

FIELD OF THE INVENTION

The present invention relates to an improved orthopaedic device, and specifically to an ankle brace for stabilizing an ankle before or after injury. In particular, the ankle brace of the present invention stabilizes the ankle against inversion and eversion and anterior subluxation while allowing normal dorsiflexion and plantarflexion movement.

BACKGROUND OF THE INVENTION

After injury to an ankle, such as a fracture or severe ankle sprain, it is often necessary to completely immobilize the injured ankle through the use of a molded plaster or resin cast. Once the injury has been stabilized, however, recovery may be accelerated by removing the molded plaster or resin east and replacing it with a removable functional walking brace so that the ankle can be exercised while healing.

Even if the injury is not severe enough to warrant complete immobilization of the ankle, it is still sometimes necessary to use a functional walking brace to stabilize the ankle against inversion (the foot rolling inward), eversion (the foot rolling outward) and/or subluxation (partial dislocation) while still allowing the normal dorsiflexion and plantarflexion movement of the ankle.

A variety of ankle braces, walking casts and other orthopaedic ankle apparatuses have previously been proposed. For instance, in my prior U.S. Pat. No. 4,977,891, granted Dec. 18, 1990, and entitled "Variable Support Ankle Brace," an ankle brace comprising two relatively rigid side supports with inflatable bladders attached to them is described. Other ankle braces including air inflatable bladders are shown in Glenn W. Johnson, Jr.'s U.S. Pat. Nos. 4,280,489 and 4,628,945. These prior art devices proposed by Johnson are intended to be worn within a separate shoe and are also inflatable.

Thermal treatment has been made available with the use of orthopaedic gel pads which tend to mold themselves to fit the area they are applied to, providing a level of comfort and padding as well as providing thermal treatment of the affected area. One such pad is shown in my U.S. Pat. No. 5,027,801.

Prior art walking braces have frequently employed rigid support shells which may engage and irritate, pinch and damage the skin within the shoe. A principal object of the present invention is to effectively avoid this problem.

SUMMARY OF THE INVENTION

In accordance with one broad aspect of this invention, the outer edge portions of at least the lower area of the side supports, adjacent to the ankle, are formed of a flexible material.

In accordance with another broad aspect of this invention, each entire side support is bonded to or integrally associated with flexible material, slightly larger in size but similar in shape to the side support. Both of these side support designs improve the fit and the comfort of the brace around the user's lower leg.

In accordance with yet another broad aspect of this invention, a more flexible material is formed around a more rigid material. In an alternative implementation, the more flexible material is formed with protrusions/tab and/or receptacles for protrusions/tabs formed in the more rigid material. This allows the more flexible material and more rigid material to be mated and interlocked to one another.

In accordance with another broad aspect of this invention, the more rigid material is hollowed out in certain areas to form a frame. The frame is covered with the more flexible material and the resultant structure is employed as an ankle brace.

Accordingly, it is a primary object of the present invention to prevent undesired inversion, eversion and anterior subluxation while allowing plantarflexion and dorsiflexion of the ankle, without irritating or pinching the skin.

Another object of this invention is to provide a more comfortable ankle brace which will firmly support an injured lower leg.

The foregoing and other features and advantages of the present invention as well as a more complete understanding thereof will be made apparent from a consideration of the following detailed description in connection with the accompanying drawings.

BRIEF DESCRIPTION OF THE DRAWINGS

FIG. 3 is a partial side view of the bladder and pump arrangement taken along lines 3—3 of FIG. 2;

FIG. 4 is a cross-sectional view of one of the main bladders taken along lines 4—4 of FIG. 3;

FIG. 5 is a cross-sectional view of one of the additional bladders and a cushioning member of the bladder taken along lines 5—5 of FIG. 3;

FIG. 7 is a perspective view of an embodiment of the ankle brace of the present invention fitted and properly secured in association with a shoe including laces;

FIG. 9 is a side view of a side support member illustrating the principles of the present invention;

FIG. 10 is a cross-sectional view of the side support taken along lines 10—10 of FIG. 9;

FIG. 11 is a side view of a different embodiment of a side support member illustrating the principles of the present invention;

FIG. 12 is a cross-sectional view of the side support of FIG. 11 taken along lines 12—12 of FIG. 11;

FIG. 13 is a side view of an alternative embodiment of a side support member of the present invention;

FIG. 14 is a cross-sectional view of the embodiment shown in FIG. 13;

FIG. 15 is a side view of an alternative embodiment of a side support member of the present invention;

DETAILED DESCRIPTION OF THE PREFERRED EMBODIMENT

Initially, it is noted that the drawings in the present case relate to two inventions, with the present invention being described in detail in connection with FIGS. 7 and 9–18. FIGS. 1–8 are included for convenience as disclosing a complete ankle support assembly as shown in FIG. 7. The embodiments of FIGS. 9–18, illustrating the principles of this invention, may be used as side supports 18, 20 in the configuration of FIG. 7.

Figure 1:
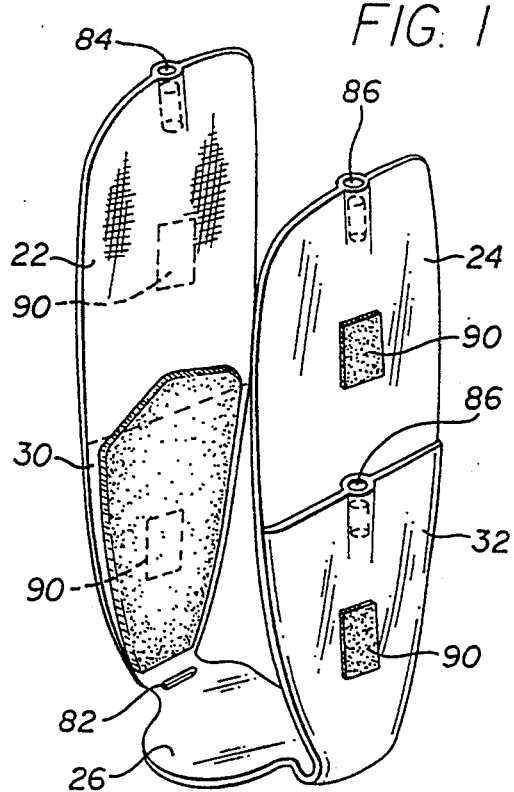
FIG. 1 is a diagrammatic, perspective view of a bladder and pump arrangement for an ankle brace.
Figure 2:
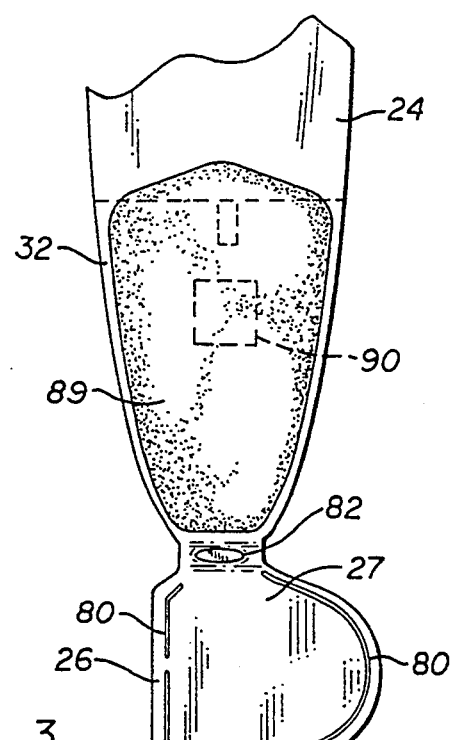
FIG. 2 is a partial unfolded top plan view of the inside surface of the bladder and pump arrangement of FIG. 1.
Figure 8:
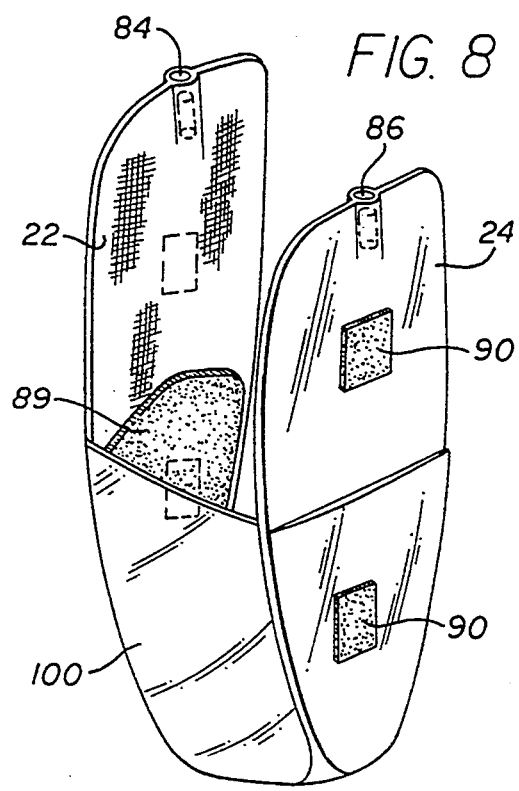
FIG. 8 is diagrammatic, perspective view of another embodiment of a bladder and pump arrangement.
Figure 6:
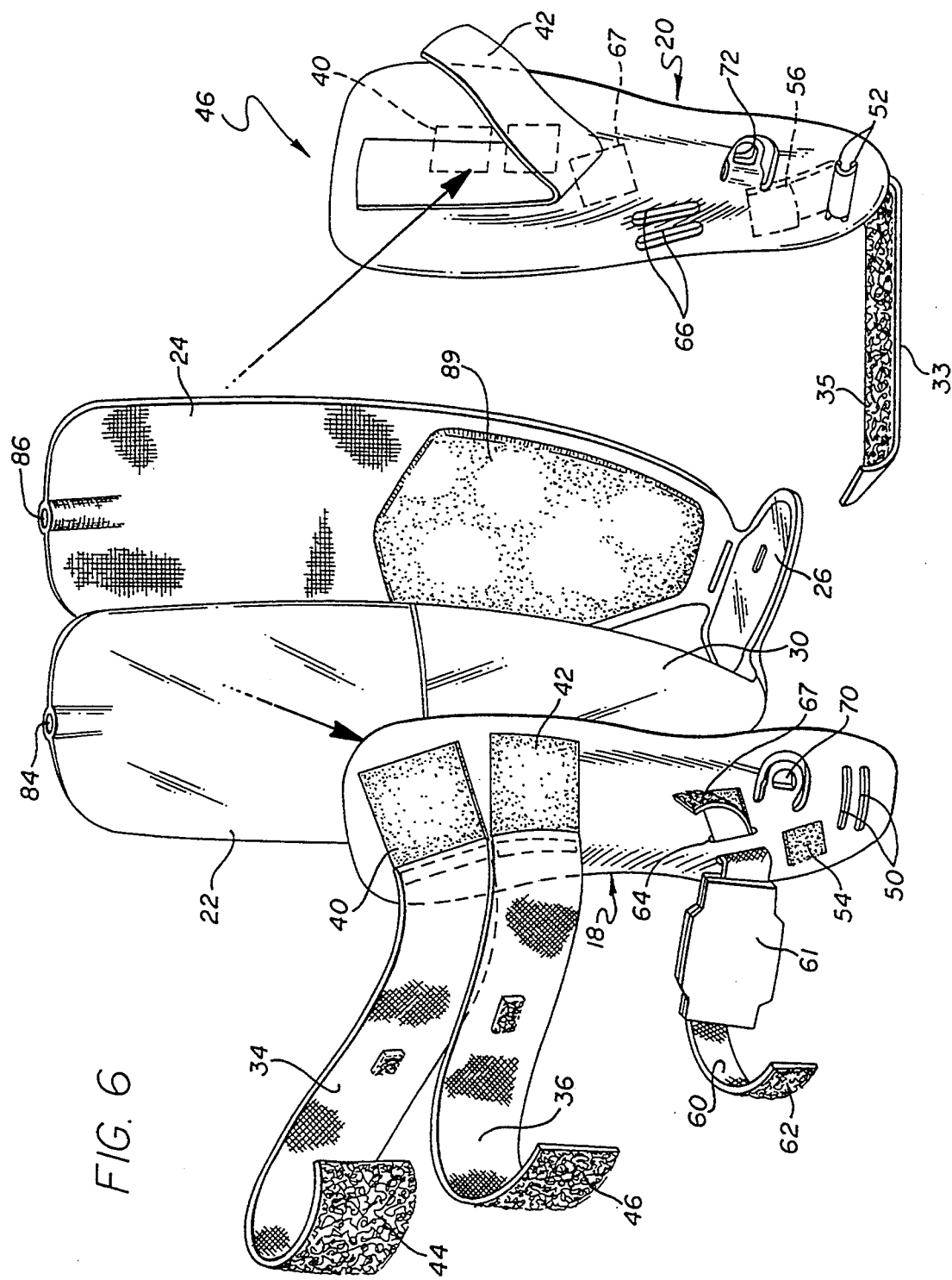
FIG. 6 is an exploded perspective view of an embodiment of an improved ankle brace.

With reference to FIGS. 6 and 7, an improved ankle brace 16 includes a pair of side support members 18 and 20 preferably made of vacuum molded plastic, for example, nylon or rigid polypropylene, having sufficient thickness and other properties so that they are relatively stiff or rigid; and they are shaped so as to fit about the lower leg and ankle and are approximately eight to ten inches long. Also included are two main inflatable bladders 22 and 24 and a pump 26 which are interconnected and formed with one welding process. The inflatable bladders 22 and 24 can be attached to the side supports 18 and 20 using a fastening fabric, such as the fabric sold under the tradename "VELCRO ®" double sided adhesive or any other suitable means. Additional inflatable bladders 30 and 32, as shown in FIGS. 1 and 2, can be placed distally upon the main inflatable bladders 22 and 24.

Interconnecting the two side support members 18 and 20 is a bottom strap 33. The bottom strap may include a surface 35 of VELCRO ® material and with the bottom strap being adjustable through the use of double openings 50 and 52 located near the bottom end of the side supports 18 and 20. The ends of the bottom strap 33 may be fixed in position with the use of additional VELCRO ® material 54 and 56 located on the outside of the side support members 18 and 20. Specifically, the adjustment is accomplished by positioning the ends of the strap 33 to extend from the outside of each support member 18 and 20 through opening 50 or 52 and then through the other one of the openings 50 or 52 and then attached by the VELCRO ® material 54. Thus, the proper distance may be easily adjusted between the side support members 18 and 20 at the lower most portion.

The side supports 18 and 20 may be securely attached around the lower leg and ankle just below the calf area using two strap members 34 and 36. These strap members 34 and 36 also include VELCRO ® portions 40 and 42 on their outer surfaces, and with VELCRO ® material 44 and 46 at the end portions of the straps 34 and 36. The VELCRO ® 40 and 42 is attached to the side support 18 or 20. As shown in FIG. 7, these straps 34 and 36 may be tightly drawn around the lower leg using the VELCRO ® material so that the ankle brace securely and firmly supports the ankle.

The ankle brace includes, in addition to the strap arrangement set forth above, a counter strap 60 which is similar in construction to the bottom strap 33. Specifically, the counter strap 60 may include a cushioning pad 61 and an inner surface covered with VELCRO ® material 62 and with the strap 60 passing through double openings 64 in the side support 18 and double openings 66 in the other side support 20. An additional piece of VELCRO ® material 67 is attached to side support member 18 and another piece of VELCRO ® material 67 is attached to side support 20. By having this arrangement the counter strap 60 may be adjusted in a similar manner to the bottom strap 33 to prevent the back portion of the side support means 18 and 20 from twisting or flexing outward at the lower end of the ankle brace 16 to compress the distal $\frac{1}{3}$ to $\frac{1}{2}$ of the brace.

The ankle brace may incorporate a lace fastening means similar to that set forth in detail in Grim, U.S. Pat. No. 4,844,094 to insure that the side supports 18 and 20 do not twist or flex outward and to more properly stabilize and compress the ankle against inversion, eversion and anterior subluxation. It is preferred, as shown in FIG. 7, that the lace fastening arrangement in the present invention comprises a hole or slot 70 and 72 integrally molded at the bottom end of each side support member 18 and 20. It is to be appreciated, however, that other attachment means such as those set forth in the U.S. Pat. No. 4,844,094 may be used.

FIGS. 1 and 2 illustrate an inflatable bladder and pump arrangement. The foot pump 26 is comprised of an open cell foam and or a flexible hollow or curved resilient material (for example, rubber, plastic, etc.) which when compressed offers an increased pressurization of the entrapped fluid within its support membranes 27. The foot pump 26 is characterized by a variety of strategically placed weld lines 80 which serve to create channels through which fluid transfer can take place between the pump 26 and the inflatable bladders 22 and 24. Other welded "darts" 82 may also be used which will aid in reducing the thickness in certain areas of the pump 26 to enhance comfort. The pump 26 may be constructed by welding in a foam of a thickness or space provided by the surrounding semi-enclosed pump material, preferably urethane or some other resilient material, whereby the foam is placed in a compressed state initially and when further compressed by the foot will be more resilient and recover quicker than if not compressed.

The foot pump 26 is approximately three and one-half inches in length and three inches in width.

In the ankle brace the two main inflatable bladders 22 and 24 are interconnected with the foot pump 26. In this case, the two bladders 22 and 24 and the pump 26 are formed with one welding process and may be considered one member but is not so limited, and may include bladders which are connected to the pump by other fluid transfer means such as with tubes or valves.

As shown in FIGS. 1, 2, 3 and 8, the main bladders 22 and 24 each have inlet valves 84 and 86 which could be flap-type valves. In such a valve, air drawn in (entering the bladders 22 and 24) forces the valve's sealing flaps, which are normally biased together, apart which allows the air to flow into the valve. Air forced in a direction opposite to the air drawn in (exiting the bladders 22 and 24) forces the flaps together and they create a substantially airtight seal. Other types of valve arrangements may be used such as an air pressure release and bleed valve or inlet valves.

Thus, as shown in FIG. 4, the main bladders 22 and 24 become inflated when air is directed through their valves 84 and 86. The bladders 22 and 24 expand a maximum width of approximately two and one-half inches. The preferred length of each main bladder 22 and 24 is approximately ten and one-half inches long and is approximately three and three-quarters inches wide. As also shown in FIG. 4, the walls 87 of bladder 22 and 24 are constructed of a non-porous resilient material such as LYCRA ® fabric coated with or bonded to a thin layer of urethane. Each wall 87 is approximately 0.015 inch (15 mills) thick and is capable of stretching under force to allow the bladders a variety of widths to accommodate a wider foot base. Further, a fabric coating 88, for example, nylon-LYCRA ®, may be laminated to the plastic film that makes up the bladders 22 and 24 to allow the skin to breathe and to increase comfort to the user. This fabric coating 88 may be approximately 0.002 inch (2 mills) thick.

FIG. 5 shows a portion of the bladder that includes additional foam padding 89 which is located at the bottom half of each main bladder 22 and 24. This padding 89 is about five inches in length and provides further comfort to the region surrounding the ankle.

As shown in FIGS. 1, 2 and 3 two more smaller inflatable bladders 30 and 32 may be placed distally upon the main inflatable bladders 22 and 24 to provide cushioning and support as well as protect the injured limb from the rigid support shell should either main bladder 22 and 24 puncture. Alternatively, these additional bladders 30 and 32 may also be made to pulsate and the longer main bladders 22 and 24 may serve as non-pulsating protective membranes. The smaller bladders 30 and 32 may be comprised of the same material and consist of the same valve arrangement as the main bladders 22 and 24.

The shorter additional bladders 30 and 32 extend from the bottom of the main bladders 22 and 24 to about halfway up towards the upper most portion of the main bladders 22 and 24. The outside surface of each bladder 22, 30, 24 and 32 has a VELCRO ® portion 90 attached to it in order to affix the support member 18 and 20 to the bladders. It should be further mentioned that all bladder arrangements 22, 30, 24 and 30, preferably, are to be distributed with a certain amount of preinflation.

FIGS. 9 through 18 illustrate the principles of this invention and show alternate side support members 18 and 20, which may be used in the assembly of FIG. 7.

FIGS. 9 and 10 show a support member 20 which is constructed of a rigid polypropylene in one embodiment. Support member 18 may be constructed in an identical manner to support member 20. The support member 20 is slightly curved (see FIG. 10) to better hug and support the ankle. One or more holes 19 for venting any heat that accumulates within the entire ankle brace 16 are also provided. Holes 19 may be used for positioning the part into a mold and also, in some cases, for mechanically securing the resilient material to the support member. The bottom perimeter of each support member 18 and 20 are covered with a flexible padded material 95, preferably vinyl, rubber, or synthetic rubber such as "SANTOPRENE ®" manufactured by Monsanto, "KRATON" manufactured by Shell, or "ALORYN" manufactured by DuPont, in order to prevent each support 18 and 20 from cutting into the user's lower leg or from puncturing the bladders 22, 23, 24 and 25, and most importantly, to improve the fit of each side support 18 and 20 around the user's lower leg. Support members 18 and 20 may be manufactured of a suitable rigid or semi-rigid material such as Nylon or Glass reinforced nylon by DuPont or High Density Polyethylene (HDPE) made by Dow Chemical Co.

Flexible resilient or padding material. 95 may be bonded to support members 18 and 20 by a permanent or semi-permanent adhesive. The flexible padded material 95 may also be formed in place around support members 18 and 20, or may be thermally bonded in place. The material 95 may, for example, be rubber or other similar material.

Openings such as slots 51 and 65 may be included in support member 20 in order to allow straps to be passed through the side support 20. In addition, slots 101, 103, 105, 107, 109, and 111, or others, may be provided to allow mechanical interlocking of the resilient or padding material 95 to secure material 95 to side support 20. Slots 101, 103, 105, 107, 109, and 111 may be replaced by suitable grooves, channels or other suitable interlocking arrangements which can be readily mated with the resilient material 95 which is positioned against side support 20.

In this manner, the resilient material and the side support may be interlocked without requiting the use of additional mechanical fasteners such as straps, tape, cement or the like. However, cement or heat bonding is preferred to supplement the mechanical interlocking.

Additionally, the inner surface of each side support 18 and 20 may include a strip or strips of VELCRO ® material 91 to allow the side supports a means of attaching themselves to the VELCRO ® portions 90 of each bladder or other padding.

FIGS. 11 and 12 show the support member 20' similar to the support member shown in FIGS. 9 and 10 except that the support is secured on top of a flexible cushioning material 95 having a slightly larger area than the side support 20 but is substantially the same shape as the side support, more securing holes 19 are present, and the strap slots 51, 65, 101, 103, 105, 107, 109, and 111 have been removed.

Alternative embodiments shown in FIGS. 13–14 and 17–18 illustrate side supports 20" and 20"', respectively similar to the side supports shown in FIG. 9–12, except that the side support is reduced in mass by forming a structural frame instead of a solid surface. The structural support consists of peripheral members 116 (FIGS. 13, 14) and 116 (FIGS. 17 and 18) which extend around the perimeter of the side support 20. Single support members 20" and 20"' are illustrated, however, the support members for the opposing side of the ankle are constructed in the same manner. In FIGS. 13 and 14 openings 110 and 112 are present in the upper and lower portions of the support member 20", and a lateral structural member 114 is located between openings 110 and 112 to told strength to the framework 116.

Figure 17:
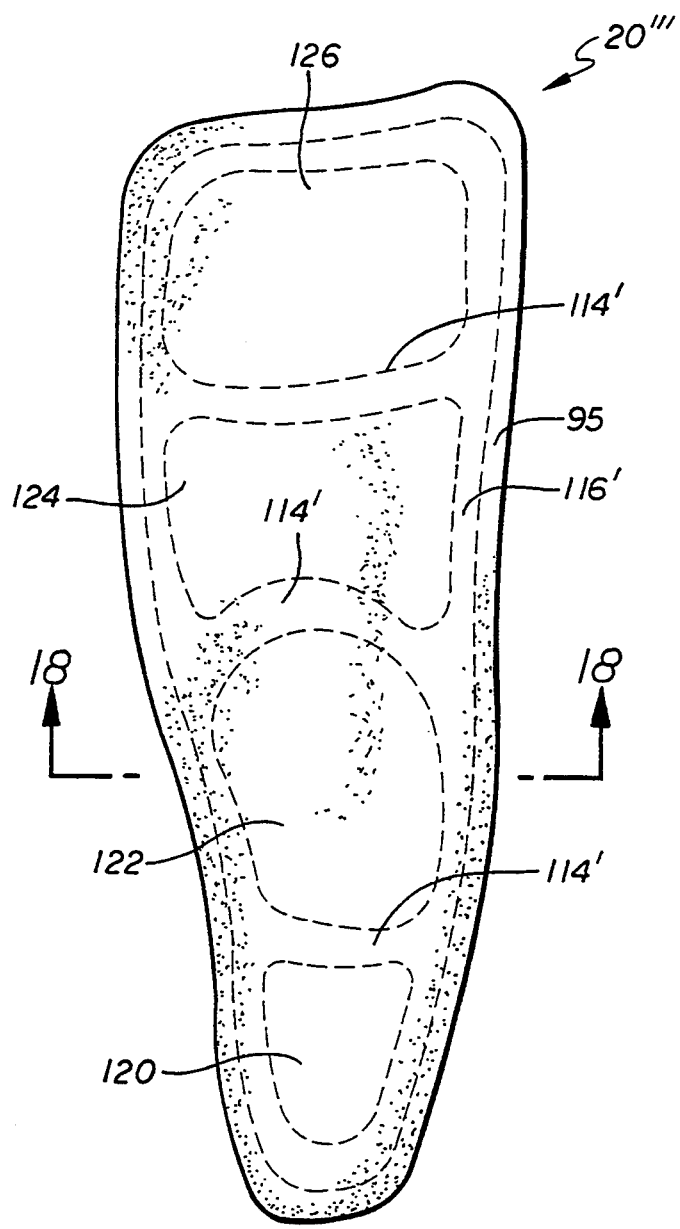
FIG. 17 is a side view of a further alternative embodiment of a side support member of the present invention.
Figure 18:
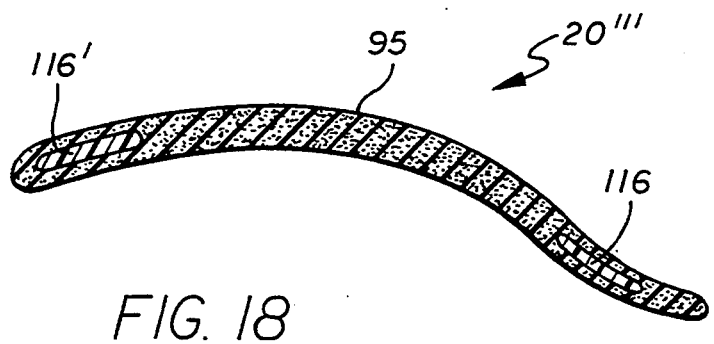
FIG. 18 is a transverse cross sectional view of the embodiment shown in FIG. 17, taken along lines 18—18 of FIG. 17.

In FIGS. 17 and 18, structural members of the three transverse members 114' add strength to the perimeter frame 116 of the side support 20"'. Thus, additional structural members can be employed to increase the structural strength and integrity of the side support 20"' without significantly increasing the weight of this support member. The configurations shown in FIGS. 13 and 17 have a weight which is reduced from the weight of side supports as shown in FIGS. 9–12, because of the material which is removed in forming openings 110, 112, 120, 122, 124, and 126. This configuration also allows the reduction in pressure in specific areas such as the malleoli or ankle bones, see area 112 in FIG. 13, and 122 in FIG. 17.

As shown in FIGS. 13 and 17, the entire perimeter of support member 20 is covered with a flexible resilient or padded material 95 in order to prevent the support members 18 and 20 from cutting into the user's lower leg, or from puncturing the bladders 22, 23, 24, and 25, and to improve the fit of each side support 18 and 20 around the user's lower leg.

It is recognized that the more rigid molded material as shown in FIGS. 9–14 may be constructed using new plastic molding techniques to include a material which is more rigid towards the center, and is extremely flexible or pliable towards the edges. This material may readily replace the use of a two piece assembly shown in FIGS. 9–18. This technique would be especially useful when employed with the configuration shown in FIGS. 9–12, wherein a more flexible, pliable layer of plastic may coat the inside surface of the side support 20 as shown in FIG. 12. This pliable material may replace the flexible material 95 in this configuration, forming a single, integral assembly which includes both a more rigid material such as a high strength reinforced plastic structural strength and a more flexible material for comfort.

Figure 16:
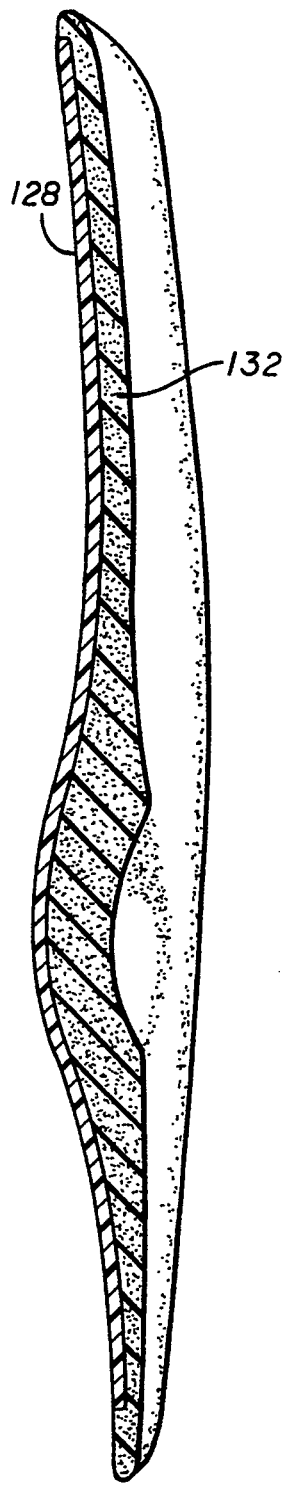
FIG. 16 is a longitudinal cross section view of the embodiment shown in FIG. 15.

In the embodiment shown in FIGS. 15 and 16, side support 128 is formed to accommodate the "bulge" of the ankle of the wearer. Flexible or resilient material 132 is shaped or formed to complement the shape of side support 128 and provide padding between the ankle of a wearer and side support 128. The showing of FIG. 15 is a view of the outside 130 of the ankle brace of FIG. 16. Flexible material 132 may be formed integrally with side support 128, or may be integrally bonded thereto, as shown in FIG. 16. The material 132 may be a soft vinyl foam of the type sold under the tradname "SANTOPRENE ®."

In the embodiments shown in FIGS. 9 and 10, a single plastic body having a more rigid central portion and grading into a more flexible plastic around the outer edges of side support 20 may be employed. This combination may eliminate the need for separate padded or resilient material 95, thereby reducing the thickness of the edges of side support 20. This may result in a side support which has a uniform thickness and is more flexible towards the edges of the side support 20 and more rigid towards the center. It is recognized that this technique may be applied to all of the edges of side support 20 in the configurations of FIGS. 9–18.

In another embodiment of the present invention, either side support 18 or 20 may be applied to the ankle of the wearer by the use of one or more straps fastening a single side support to the leg of the user. This configuration can be successfully employed to treat less severe ankle injuries while reducing the weight and bulkiness of the brace which must be worn by the user. Preferably the side support is located on the side of the leg of the wearer to provide the greatest support to the ankle, and immobilize the ankle against particular undesired rotation based on the nature of the ankle injury.

For many users, it is additionally desirable to place a padded material between the ankle and the straps that surround the lower leg, holding the side support 18 or 20 against the lower leg of the wearer.

The operation of the ankle brace 16 in conjunction with air bladders would be as follows: the bladder and pump arrangement is to be attached to the inside of the side supports 18 and 20. If the brace 16 has been previously used, the bottom strap 33 and the counter strap 60 would already have been adjusted. If not, the wearer would position the side supports 18 and 20 to both sides of the ankle, and then after the side supports 18 and 20 are properly positioned, the ankle brace 16 would be held in place using the strap members 34 and 36. The bottom strap 33 would then be adjusted by peeling the VELCRO ® material 35 back from the corresponding VELCRO ® 54 and 56 and pulling up both sides of the strap 33 until the bottom of the side supports are firmly in position. The ends of the strap 35 would then be firmly pressed down on the VELCRO ® 54 and 56 to lock the strap in 33 in position. Similarly the counter strap 60 would be adjusted to pull the back lower end of the side supports 18 and 20 together above the heel.

The shoe would now be fitted over the entire ankle brace 16, as shown in FIG. 7, and the laces laced through the holes 70 or in other fastening means located at the lower end of the side supports 18 and 20. The laces would then be pulled tightly and tied, again as shown in FIG. 7, so that the ankle brace 16 is firmly in position.

Subsequently the bladders 22, 30, 24 and 32 are inflated to their therapeutically desired pressure by using, for example, an attachable hand-held pump.

Therefore, while in use, the fluid within the pressurized ankle support bladders 22, 30, 24 and 32 and the interconnected preinflated foot pump is displaced back and forth between either the main bladders 22 and 24 and/or the shorter bladders 30 and 32 thereby creating a pulsing action which lends to a massaging compression effect that helps reduce swelling and atrophying and increases venous and lymphatic return throughout the lower leg while effectively preventing inversion, eversion and anterior subluxation of the ankle.

While FIGS. 1–8 relate to the combination using bladders, it is to be understood that the arrangements of FIGS. 9–18 may be employed using gel or foam rubber pads, for example, between the side members and the ankle, or in some cases with no additional padding.

Although the invention has been described with reference to particular embodiments, it is to be appreciated that other adaptations and modifications may be used without departing from the spirit and scope of the present invention. For example, in FIG. 8 a heel cup 100 which may or may not be inflatable may be included to provide further support to the ankle region. Also, a possible extra bladder surrounding the ankle may be incorporated into the brace 16 to contain gel or water, with or without foam, for hot or cold therapy.

Accordingly, the present invention is not limited to the constructions precisely as shown in the drawings or described in the detailed description.

What is claimed is:

1. An improved ankle brace for restraining the ankle against inversion and eversion while allowing for plantar flexion and dorsiflexion, comprising:
   a pair of substantially rigid side supports having upper and lower ends, preformed of a relatively rigid material to conform to the shape of the lower leg, for fitting about the lower leg, said side supports having a configuration to encase both sides of the ankle, the lower end of the side supports having a reduced size as compared to the upper end of the side supports, allowing for insertion into the sides of the shoe;
   said side supports having a flexible resilient material of a formed shape which is contoured to mechanically interfit with and extend beyond outer perimeters of said side supports to improve the fit of said side supports around the user's lower leg and protect the wearer from injury or skin irritation from the edges of said supports.

2. An improved ankle brace as defined in claim 1 wherein the perimeter of the lower end of said side supports are, covered with said flexible resilient material.

3. An improved ankle brace as defined in claim 1 wherein each side support is mounted on top of said flexible resilient material, said flexible material having a slightly larger area than said side support and having substantially the same shape as said side supports.

4. An improved ankle brace for insertion into a shoe, for restraining the ankle against inversion and eversion, while allowing for plantar flexion and dorsiflexion, comprising:
   at least one substantially rigid side support for fitting about at least a portion of the lower leg and having upper and lower portions, the side support oriented in a configuration to support the affected side of the ankle; and
   flexible resilient material of a formed shape which is contoured to mechanically interfit with and substantially covering at least a portion of outer edges of said side support.

5. An improved ankle brace as defined in claim 4 in which said flexible resilient material is thermally bonded to said side supports.

6. An improved ankle brace as defined in claim 4 wherein said flexible resilient material covers at least the edges of the lower portion of said side supports.

7. An improved ankle brace as defined in claim 4 and further comprising:
   additional padding means secured to the inside of said side supports to provide further comfort to the region surrounding the ankle.

8. An improved ankle brace as defined in claim 4 wherein the lower ends of said side supports can be inserted into the sides of a shoe with laces; and
   including fastening means located on the side supports to receive the laces of the shoe so that the laces can be tightened and tied to immobilize the ankle.

9. An improved ankle brace for insertion into a shoe, for restraining the ankle against inversion and eversion, while allowing for plantar flexion and dorsiflexion, comprising:
   two substantially rigid side supports for fitting about the lower leg on both sides, and having upper and lower portions, the side supports being oriented in a configuration to support both sides of the ankle;
   flexible resilient material integrally secured to and substantially covering at least a portion of outer edges of said side supports;
   inflatable main bladders mounted on an inner surface of said side supports to provide supporting pressure, and for providing a cushion between the ankle and the side supports;
   a preinflated resilient foot pump interconnected between said main bladders;
   said inflatable main bladders and said pump being formed integrally with one another;
   another shorter inflatable bladders mounted distally upon said main bladders; and
   said foot pump having strategically placed weld lines serving to create channels through which fluid transfer can take place between the pump and the additional shorter inflatable bladders;
   whereby walking or running activity increases the fluid pressure in said additional shorter inflatable bladders and provides additional support to the foot and ankle against inversion, and eversion while creating a pulsing action which lends to a massaging compression effect.

10. An improved ankle brace for insertion into a shoe, for restraining the ankle against inversion, and eversion while allowing for plantar flexion and dorsiflexion, comprising:
   a pair of substantially rigid side supports having upper and lower ends, preformed of a relatively rigid material to conform to the shape of the lower leg, for fitting about the lower leg and with said side supports having a configuration to encase both sides of the ankle and with the lower end of the side supports for insertion into the sides of the shoe;
   means for securing the side supports to firmly encase the ankle;
   said securing means including a counter strap extending between the side supports at a lower position just above the heel near an intermediate point at the ankle, and fastening means located on the side supports substantially at an elevation at or immediately below said intermediate point and substantially at the level of the ankle joint to receive the laces of the shoe so that the laces can be tightened and tied to immobilize the ankle against inversion, eversion while permitting plantar flexion and dorsiflexion; and
   a flexible cushioning material of a formed shape which is contoured to mechanically interfit with and surround edges of said side supports to improve the fit of each side support around the lower leg extremity, and protect the wearer from the edges of said side supports.

11. An improved ankle brace as defined in claim 10 wherein the securing means includes an adjustable bottom strap for extending between the side supports at a bottom position within the shoe.

12. An improved ankle brace as defined in claim 10 in which said flexible cushioning material is thermally bonded to said side supports.

13. An improved ankle brace as defined in claim 10 and further comprising:
   one or more inflatable bladders mounted on and secured to an inner surface of said side supports to provide supporting pressure, and for providing a cushion between the ankle and the side supports, said bladders distributed with a certain amount of preinflation;
   a preinflated resilient foot pump fluidically interconnected between said bladders;
   said foot pump constructed of a resilient material which when compressed offers an increased pressurization of entrapped fluid within said bladders and having strategically placed fluid lines serving to create channels through which fluid transfer can take place between the pump and the inflatable bladders; and
   said inflatable bladders each including a one-way inlet valve for supplying fluid to the bladders and a relief means for releasing fluid from said inflatable bladders;
   whereby walking or running activity increases the fluid pressure in said inflatable bladders and provides additional support to the foot and ankle against inversion, and eversion while creating a pulsing action which lends to a massaging compression effect.

14. An improved ankle brace as defined in claim 10 wherein said ankle brace includes an additional bladder containing gel or fluid for providing hot or cold therapy.

15. An improved ankle brace for insertion into a shoe, for restraining the ankle against inversion, and eversion while allowing for plantar flexion and dorsiflexion, comprising:

at least one substantially rigid side support for fitting about the lower leg and having upper and lower portions, the side support having a configuration to support the affected side of the ankle;

said side support having a stiff or semi-rigid structural portion and resilient cushioning material of a formed shape which is contoured to interfit with said structural portion, said resilient cushioning material forming edges of at least a portion of said support.

16. An improved ankle brace as defined in claim 15 wherein said structural portion has a peripheral frame, and said resilient cushioning material extends across said frame and beyond the outer periphery thereof.

17. An ankle brace comprising:

a pair of side supports having upper and lower ends, to generally conform to the shape of the lower leg, for fitting about the lower leg, said side supports having a configuration to encase both sides of the ankle, allowing for insertion within the sides of a shoe;

said side supports having a combination of selectively different flexural properties, whereas the more flexible material is adjacent to the ankle and forms at least the outer parameter distal portion of the shell and the more rigid material is positioned more centrally for flexural strength to prevent eversion and inversion of the ankle;

said side supports both comprised of at least two thermoplastic materials varying in durometric stiffness including a softer material forming outer edges of at least part of the support and a more rigid material located more centrally for flexural strength to resist eversion and inversion of the ankle; and said softer material being of a formed shape which is contoured to interfit with said rigid material to prevent separation of said two materials during the rigors of athletic endeavors.

18. The device as described in claim 17 in which said side supports are comprised of a rigid material and a molded contoured lower durometer material affixed to said rigid material.

19. The device as described in claim 17 in which said side supports consist of a rigid material, said rigid material having upper and lower ends shaped to generally conform to the lower leg and a molded, contoured lower durometer material affixed to said rigid material to provide a unit which resists inversion and eversion of the ankle.

20. The device as described in claim 17 in which said rigid material is affixed to a lower durometer material, said lower durometer material determining the shape of the shell and being preformed with recesses to mate with the shape of the rigid material to form a unitary support which resists inversion and eversion.

21. An improved ankle brace for insertion into a shoe, for restraining the ankle against inversion and eversion, while allowing for plantar flexion and dorsiflexion, comprising:

at least one substantially rigid side support for fitting about at least a portion of the lower leg and having upper and lower portions, the side support oriented in a configuration to support the affected side of the ankle;

flexible resilient material contoured to mechanically interfit with and substantially covering at least a portion of outer edges of said side support;

an inflatable main bladder mounted on an inner surface of said side support;

an additional shorter bladder mounted on said main bladder; and a foot pump operationally connected to said shorter bladder to increase a pressurization of said shorter bladder in response to a walking or running activity.

* * * * *